(12) United States Patent
Bruder et al.

(10) Patent No.: US 7,130,369 B2
(45) Date of Patent: Oct. 31, 2006

(54) IMAGING TOMOGRAPHY APPARATUS WITH TWO ACQUISITION SYSTEMS IN DIFFERENT PLANES AND METHOD FOR DETERMINING POSITION CORRECTION VALUES FOR THE PLANES

(75) Inventors: Herbert Bruder, Höchstadt (DE); Martin Petersilka, Adelsdorf (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/166,969

(22) Filed: Jun. 24, 2005

(65) Prior Publication Data

US 2006/0018426 A1    Jan. 26, 2006

(30) Foreign Application Priority Data

Jun. 24, 2004  (DE)  ....................  10 2004 030 549

(51) Int. Cl.
*G01N 23/00*  (2006.01)
(52) U.S. Cl. .......................................... 378/9; 378/207
(58) Field of Classification Search .................... 378/9, 378/207
See application file for complete search history.

(56) References Cited

U.S. PATENT DOCUMENTS

| 4,384,359 | A |  | 5/1983 | Franke |
| 4,991,190 | A |  | 2/1991 | Mori |
| 6,421,412 | B1 | * | 7/2002 | Hsieh et al. ................... 378/9 |
| 6,866,419 | B1 | * | 3/2005 | Toth .......................... 378/207 |

FOREIGN PATENT DOCUMENTS

| DE | 29 16 848 | 11/1979 |
| DE | 196 15 456 | 10/1997 |

* cited by examiner

*Primary Examiner*—Edward J. Glick
*Assistant Examiner*—Hoon Song
(74) *Attorney, Agent, or Firm*—Schiff Hardin LLP

(57) ABSTRACT

In a tomography apparatus and method for obtaining correction values for two measurement planes, wherein the tomography apparatus an acquisition system disposed in a first measurement plane and a second acquisition system disposed in a second measurement plane that are disposed in the azimuthal direction around a common rotation axis, position correction values for both measurement planes are determined for a substantially constant rotation angle speed of the two acquisition systems using measurement values calculated at a rotation angle position of a reference object that can be introduced into both measurement planes. An artifact-free reconstruction of a slice or volume image can be made using the position correction values.

26 Claims, 3 Drawing Sheets

IMAGING TOMOGRAPHY APPARATUS WITH TWO ACQUISITION SYSTEMS IN DIFFERENT PLANES AND METHOD FOR DETERMINING POSITION CORRECTION VALUES FOR THE PLANES

BACKGROUND OF THE INVENTION

1. Field of the Invention

The present invention concerns an imaging tomography apparatus of the type having at least a first acquisition system disposed in a first measurement plane, with a first radiator and a first detector for generation of detector output signals that are a measure of the absorption of the radiation emanating from the first radiator, and a second acquisition system disposed in a second measurement plane, with a second radiator and a second detector for generation of detector output signals that are a measure of the absorption of the radiation emanating from the second radiator, whereby both acquisition systems are mounted to rotate around a common rotation axis. The invention moreover concerns a method for such a tomography apparatus for determination of the relative positions of both acquisition systems.

2. Description of the Prior Art

A tomography apparatus with only one acquisition system is known from German OS 196 15 456 wherein, for correction of image distortions in the reconstructed images, an incorrect angle position between the measurement plane of the acquisition system and the patient table plane is detected.

In contrast to this, German OS 29 16 848 discloses a tomography apparatus with a number of acquisition systems. The acquisition systems are mounted such that they can be adjusted in the direction of the rotational axis so that, depending on the arrangement, alternatively a high scanning speed or scanning of a number of adjacent slices per rotation can be achieved.

A tomography apparatus with a number of acquisition systems is likewise known from German OS 29 51 222, wherein a grid-controlled x-ray tube that is contained in a separate housing together with the filament transformer is used as the x-ray radiator for fast activation and deactivation of an x-ray beam.

Other tomography apparatuses with at least two acquisition systems are known, for example, from U.S. Pat. Nos. 4,991,190 and 6,421,412. The advantage of such tomography apparatuses with a number of acquisition systems compared to an apparatus with a single acquisition system is the capability to examine a subject with an increased sampling speed or with an increased sampling resolution. A high sampling speed is of importance when movement artifacts that are caused by voluntary or involuntary movements of the subject (for example of an organ of an organism to be examined) must be minimized in the reconstructed image. In the examination (for example of a heart), for reconstruction of an artifact-free slice or volume image it is necessary that all exposures used for the reconstruction optimally record the same movement state (phase) of the heart at the various rotation angle positions.

In addition to single image acquisition, entire sequences of slice or volume images are generated for representation of movement cycles for medical examinations. A higher sampling speed thereby offers the advantage of an improved temporal resolution of the imaged region affected by a movement cycle so that rapidly-changing movement states can be acquired.

A tomography apparatus with a number of acquisition systems also can be operated such that a higher sampling resolution is achieved compared to a tomography apparatus with only one acquisition system. This is particularly of importance when organs or organ parts of an organism must be resolved in a small examination volume, as is the case, for example, for an examination of blood vessels.

In a tomography apparatus with a number of acquisition systems, the acquired detector output signals of the various acquisition systems are combined with one another for reconstruction of a slice or volume image, both in the operating mode to increase the sampling speed and in the operating mode to increase the sampling resolution. The reconstruction of a slice or volume image from data of various acquisition systems thereby always ensues based on the prior knowledge of the position of the first measurement plane relative to the position of the second measurement plane.

SUMMARY OF THE INVENTION

An object of the present invention is to provide a device and a method for an imaging tomography apparatus of the type initially described that allow the position of the first measurement plane of the first acquisition system to be determined in a simple manner relative to the second measurement plane of the second acquisition system.

According to the invention, this object is achieved by an imaging tomography apparatus and method wherein position correction values are determined using a reference object that can be positioned in both measurement planes of the acquisition systems and wherein, from the detector output signals of the first detector, a measurement value associated with the first detector is calculated for at least one substantially constant rotation angle speed of both acquisition systems at at least one rotation angle position and, from detector output signals of the second detector, a measurement value associated with the second detector is calculated for the position of the reference object mapped (imaged) in the respective detector. The position correction values for the measurement planes of both acquisition systems are determined based on the measurement values calculated in this manner.

Ideally the tomography apparatus is adjusted such that both measurement planes are identical, i.e. such that the measurement planes of both acquisition systems are aligned in parallel and coincide in terms of their position along the rotational axis in the z-direction. The invention proceeds from the recognition that the ideal alignment of the measurement planes of both acquisition systems can be displaced due to installation tolerances in the manufacturer process and due to strong acceleration forces at high rotational speeds in the operation of the tomography apparatus. Deviations in the parallelism of the two measurement planes and/or an offset of the two measurement planes along the system axis in the z-direction (z-offset) are normally dependent on the magnitude of the rotational speed or on the rotational forces acting on the acquisition systems. Such deviation from the ideal situation causes image errors (artifacts), which lead to a general worsening of the achievable image quality, in the reconstruction of a slice or volume image.

An improvement of the slice or volume images generated from the detector output signals is achieved by the determination of position correction values, allowing the position relation of the two measurement planes to be taken into consideration in the reconstruction.

The determination of the position correction values for the measurement planes of the two acquisition systems is cost-effective and can be particularly simply implemented in a calibration process, since only an evaluation of the detector output signals of both acquisition systems must be made for the reference object introduced into the measurement region. The position correction values of the acquisition systems can also be determined for various rotation speeds and thus for any operating mode of the tomography apparatus.

At any (arbitrary) rotation angle position of the two acquisition systems, the position correction values can be determined, by means of the reference object that can be positioned on the rotation axis of the two acquisition systems, from a difference of a measurement value associated with the first detector and a measurement value associated with the second detector. The difference of the two measurement values thereby yields a displacement vector, independent of the rotation angle position of the two acquisition systems, which represents a z-offset of the first measurement plane relative to the second measurement plane. By taking the position correction data that can be determined in such a manner into account in the reconstruction of a slice or volume image, errors in the resulting image also can be prevented in a simple manner given a z-offset of both measurement planes.

In a further embodiment of the invention, the position correction values can be determined at respectively determined rotation angle positions of the acquisition systems using the reference object that can be positioned outside of the rotation axis of the two acquisition systems, and from differences of measurement values associated with the first detector and of measurement values associated with the second detector. Depending on the position of the first measurement plane relative to that of the second measurement plane, the difference of two measurement values is dependent on the respective rotation angle position of the two acquisition systems, or dependent on which detector elements of a detector the reference object has been mapped.

The difference of the two measurement values, dependent in this manner on the position of the detector element in the respective detector, yields a displacement vector that describes both a z-shift and a tilting of the two measurement planes around the imaginary connecting line "first radiator-rotation axis" or "second radiator-rotation axis." In reconstruction of a slice or volume image, errors in the resulting image can be prevented in a simple manner using the position correction values that can be determined in this manner and that are dependent on the detector elements.

So that the projection image of the reference object on the detectors of both acquisition systems is independent of the rotation angle positions of the acquisition systems, and so that a simple evaluation of the detector output signals is possible, the reference object can exhibit a rotationally symmetrical design.

In an embodiment the calculation of the measurement value associated with the respective detector or of the detector element position on which the reference object is mapped is possible in a manner that is relatively insensitive to noise in the detector output signals, by the reference object being imaged on a number of detector elements. The position is determined from the detector output signals in the sense of an intensity focal point.

In order to enable immediate access to the position correction values of both measurement planes of the acquisition systems during the normal operation for examination of a patient, in an embodiment of the invention a memory is provided in which the determined position correction values can be stored for a number of different, substantially constant rotation angle speeds.

DESCRIPTION OF THE PREFERRED EMBODIMENTS

Figure 1:
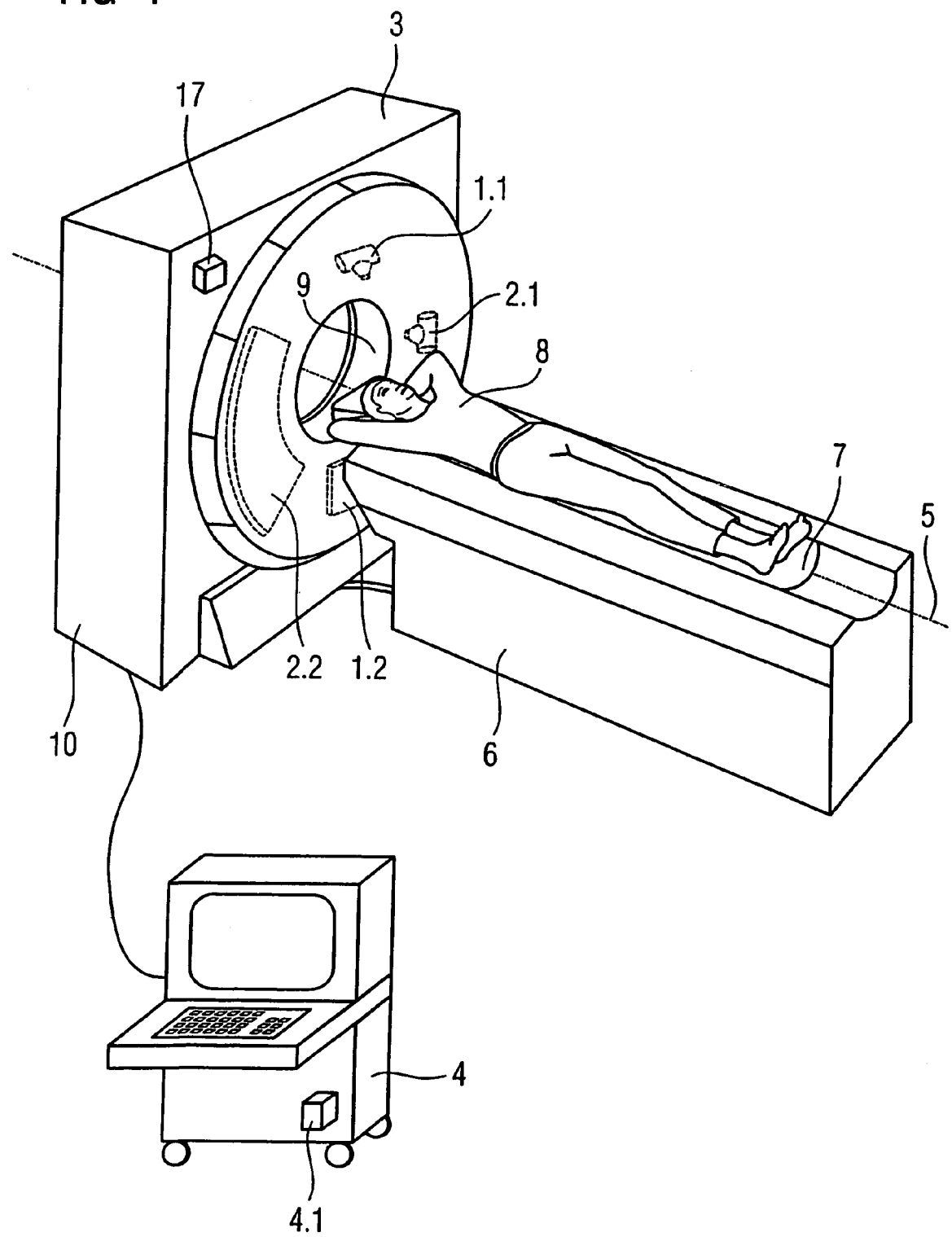
FIG. 1 shows a tomography apparatus according to the invention in a perspective view.

FIG. 1 shows an inventive imaging tomography apparatus 3, in the form of an x-ray computed tomography apparatus, with a patient bed 6 for acceptance and supporting of a patient 8. The patient bed 6 has a movable table plate 7 by means of which the patient 8 can be moved through an opening 9 in the housing 10 of the tomography apparatus 3 into the examination or scan region. Moreover, a continuous axial feed of the table plate 7 is effected during a spiral scan.

A gantry (measurement carriage; not visible in FIG. 1) that can be rotated with a high speed around a rotational axis 5 proceeding through the patient 8 is located within the tomography apparatus 3.

Two acquisition systems are mounted on the gantry to achieve a high scanning speed or a high scan resolution. The first acquisition system has an x-ray tube as a first radiator 1.1 and an M-row and N-column x-ray detector array as a first detector 1.2. The second acquisition system has a separate x-ray tube as a second radiator 2.1 and a separate M-row and N-column x-ray detector array (structurally identical to the first x-ray detector array) as a second detector 2.2. Both acquisition systems are mounted at fixed positions, offset by 90° in the azimuthal direction around the rotational axis 5.

The x-ray detector arrays are, for example, based on an electronically-readable scintillator ceramic, known as a UFC ceramic, and are used for generation of detector output signals that are a measure of the absorption of the radiation emanating from the corresponding radiator 1.1 or 2.1 and passing through the measurement region. Other detectors, for example large area detectors with 256 or more rows, also can be used for generation of detector output signals.

The detector output signals of both acquisition systems scanning at different rotation angle positions are processed in a control and image computer 4 (associated with the tomography apparatus 3) into a slice or volume image by means of an image reconstruction algorithm. The detector output signals of both acquisition systems are initially merged ("mixed") into a common projection or raw data set. The operation of the tomography apparatus 3 by a physician or technician or the like likewise ensues from the control and image computer 4. The control and image computer 4 additionally has a calculation unit 4.1 for determination of the position correction values.

Figure 2:
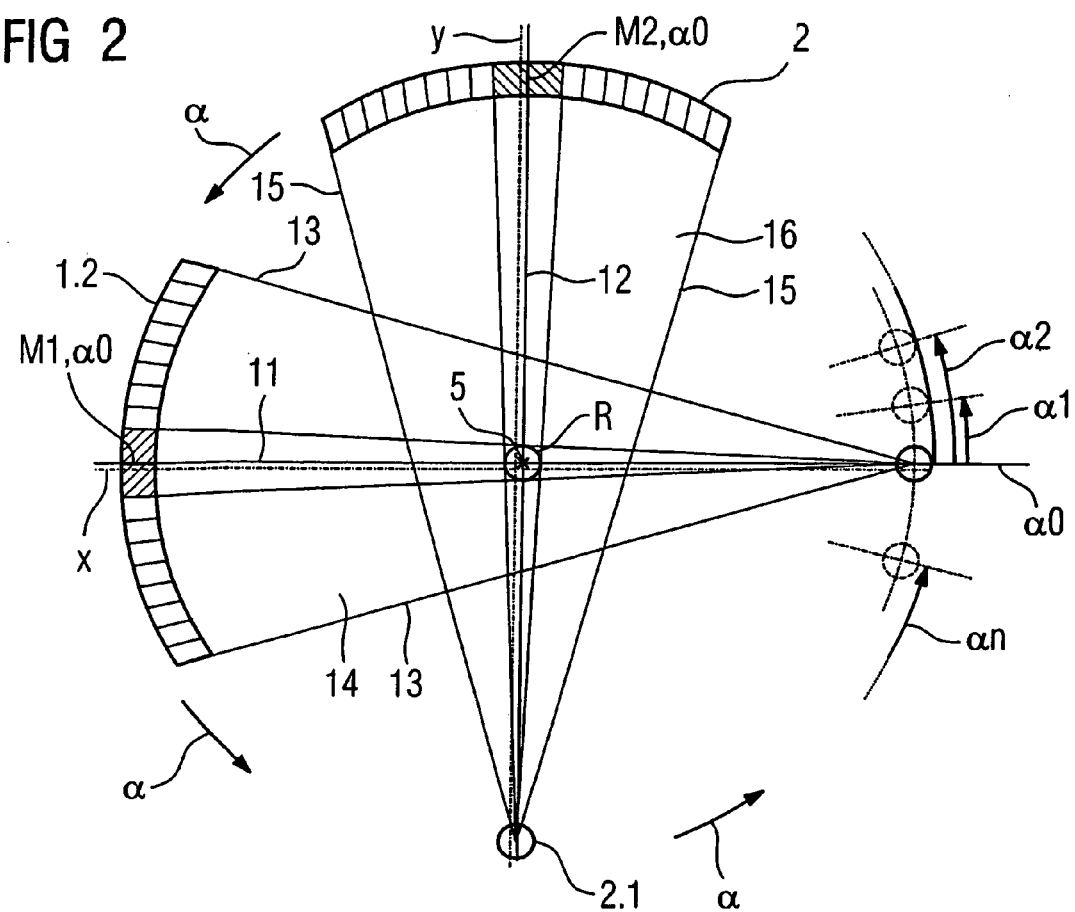
FIG. 2 shows a cross-section of two acquisition systems of the tomography apparatus of FIG. 1, with a reference object positioned on the rotational axis.

FIG. 2 shows both acquisition systems of FIG. 1 with an exemplary reference object R positioned on the rotation axis 5 in a cross-section representation.

Both acquisition systems are mounted such that they can rotate in the azimuthal direction around a common rotation axis 5 in the indicated rotation angle direction α.

A first measurement plane 14 of the first acquisition system is spanned by an x-ray beam emanating from the first radiator 1.1 and striking the detector 1.2, with edge rays 13 and a first center ray 11. In a corresponding manner, a second measurement plane 16 of the second acquisition system is spanned by an x-ray beam emanating from the radiator 2.1 and striking the detector 2.2, with edge rays 15 and a second center ray 12.

Rows of the detectors 1.2, 2.2 are respectively shown in cross-section representation with multiple respective detector elements for the generation of detector output signals. A first measurement value M1, α0 can be calculated from the detector output signals of the first detector 1.2 generated by projection of the reference object R and a corresponding second measurement value M2, α0 can be calculated from the detector output signals of the second detector 2.2. The measurement value M1, α0 and M2, α0 represent the position of the detector element on which the reference object R is projected in the respective detector 1.2 or 2.2.

In an embodiment of the invention, the measurement values M1, α0, M2, α0 for a reference object R positionable on the rotation axis 5 can be calculated at at least one rotation angle position α0 of both acquisition systems by the calculation unit 4.1 (shown in FIG. 1). The position correction values, for example, can be represented by displacement vectors that describe the mutual offset of respective, identically arranged detector elements in the first detector 1.2 and in the second detector 2.2. By the positioning of the reference object R on the rotation axis 5 of both acquisition systems, the position correction values for a z-offset of both measurement planes 14, 16 can be determined from the measurement values M1, α0, M2, α0 at an arbitrary rotation angle position of the acquisition systems. The z-offset of the projection images mapped in the detectors 1.2, 2.2 thus can be individually compensated for each detector element. The determination of the position correction values ensues for any rotation angle speed of the gantry that is substantially constant.

Figure 3:
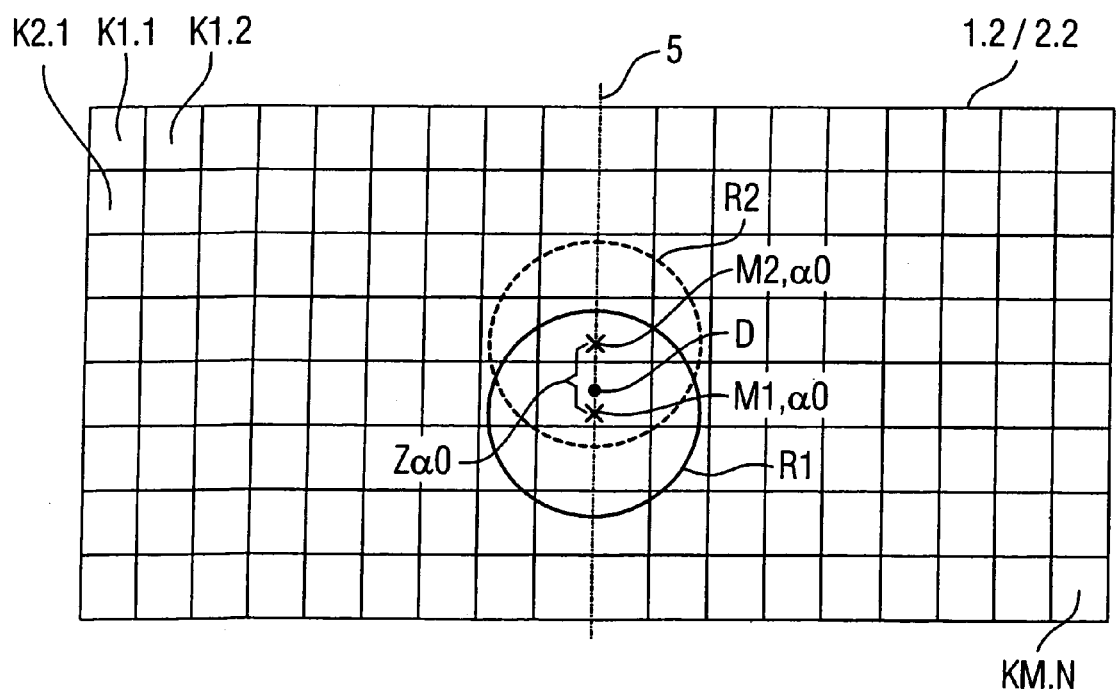
FIG. 3 shows superimposed projection images of the reference object at a rotation angle position given a z-offset of the measurement planes shown in FIG. 2.

FIG. 3 as an example shows in a common image the first projection image R1 of the reference object R, the first projection image R1 being associated with the first detector 1.2 and the second projection image R2 of the registration object R, the second projection image R2 being associated with the second detector 2.2, for an arrangement (shown in FIG. 2) of the reference object R, wherein both acquisition systems and thus both measurement planes 14, 16 are aligned in parallel, but displaced in the z-direction along the system axis 5. The projection images of both detectors 1.2, 2.2 are thereby superimposed such that respective identically-arranged detector examination subject of both detectors come into congruence. Due to the z-offset relative to the second projection image, the first projection image R1 is mapped at a different position in the direction of the system axis 5.

The measurement values M1, α0, M2, α0 can be inventively calculated by the calculation unit 4.1 from the detector output signals of the respective detector 1.2 and 2.2. The measurement values M1, α0, M2, α0 thereby represent the position of the detector element on which the reference object R is mapped in the respective detector 1.2 or, respectively, 2.2.

A robust calculation (relative to detector noise) of the measurement value M1, α0 or M2, α0 can be implemented when the reference object R can be imaged on a number of detector elements, as shown in FIG. 3.

If the reference object R has a rotationally-symmetrical design, this enables a particularly simple determination of the measurement values M1, α0, M2, α0 that can be calculated in a short time because the image of the reference object R projected in the detectors is independent of the rotation angle position of both acquisition systems. Such a reference object R is, for example, in the form of a sphere.

The calculation of the measurement values M1, α0, M2, α0 preferably ensues on the basis of the detector output signals by the calculation of an intensity focal point. In the simplest case the detector output signals of the detector elements are separately weighted (multiplied) according to the position designated by row and column coordinates within the detector array, are added together and divided by the number of the added values (M×N) for this purpose. The measurement value M1, α0 and M2, α0 that can be calculated from this weighting represents the position of the detector element on which the reference object R is imaged in the respective detector 1.2 or 2.2 with a precision of sub-pixel units.

The determination of the position correction values K1.1 . . . KM.N ensues from a difference Zα0 of the measurement value M1, α0 associated with the first detector 1.2 and of the measurement value M2, α0 associated with the second detector 2.2. The difference Zα0 represents a displacement vector with which the z-offset of acquisition systems aligned in parallel to one another, or the measurement planes 14, 16, can be corrected for each detector element. The difference Zα0 is independent of the selected rotation angle position for the reference object R that can be positioned on the rotation axis 5. For example, as noted above, the position correction values can be represented by displacement vectors that describe the mutual offset of respective, identically arranged detector elements in the first detector 1.2 and in the second detector 2.2. For the case of acquisition systems aligned in parallel but offset in the z-direction, the position correction values are identical for all detector elements.

Due to installation tolerances and strong acceleration forces given rotation of both acquisition systems, both measurement planes 14, 16 of the acquisition systems may be additionally tilted around the imaginary connecting line "first radiator 1.2-rotation axis 5" or "second radiator 2.2-rotation axis 5". In this case the position correction values K1.1 . . . KM.N can be determined according to an embodiment of the invention (shown in FIG. 4) with the reference object R positioned outside of the rotation axis 5, from measurement values M1, α0, . . . M1, an, M2, α0 . . . M2, an that can be calculated at specific rotation angle positions α0, α1, . . . an of both acquisition systems, examples of which are shown in FIG. 4.

Figure 4:
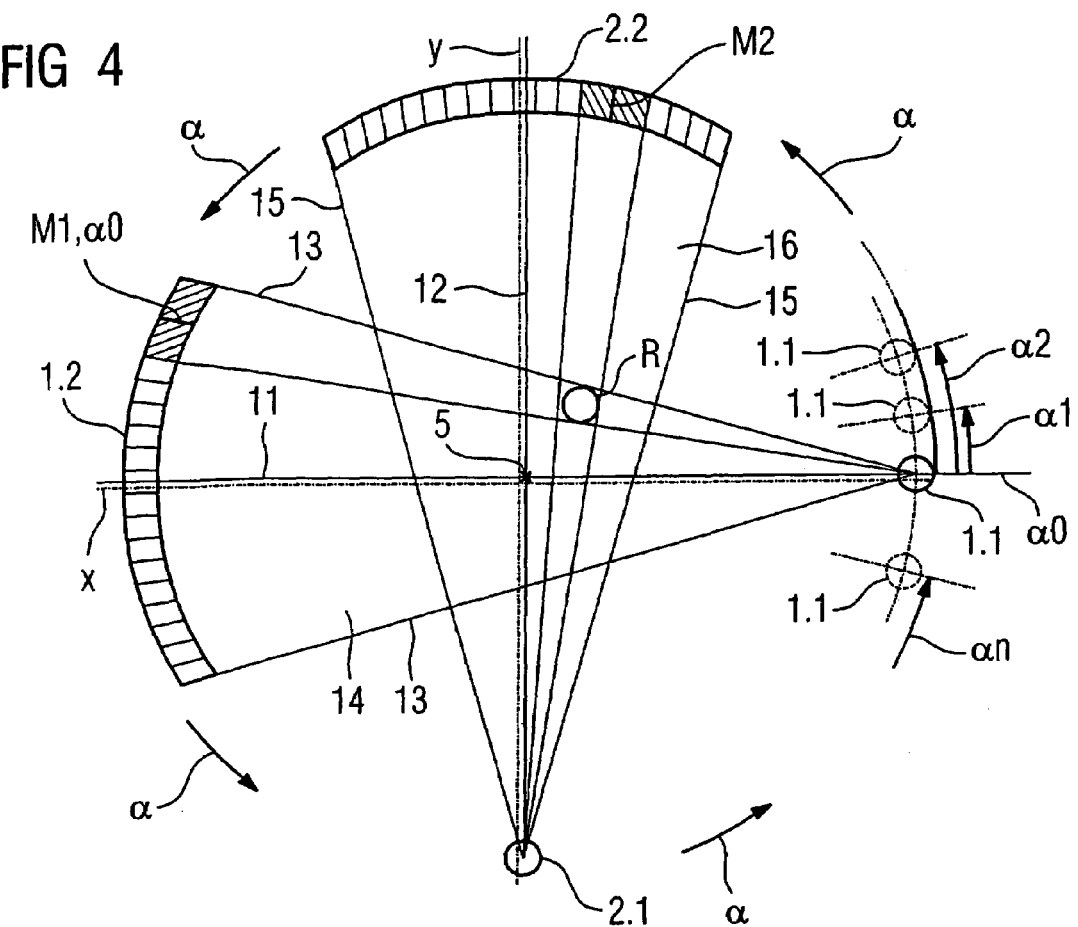
FIG. 4 shows a cross-section of two acquisition systems of the tomography apparatus of FIG. 1 with a reference object positioned outside of the rotational axis.
Figure 5:
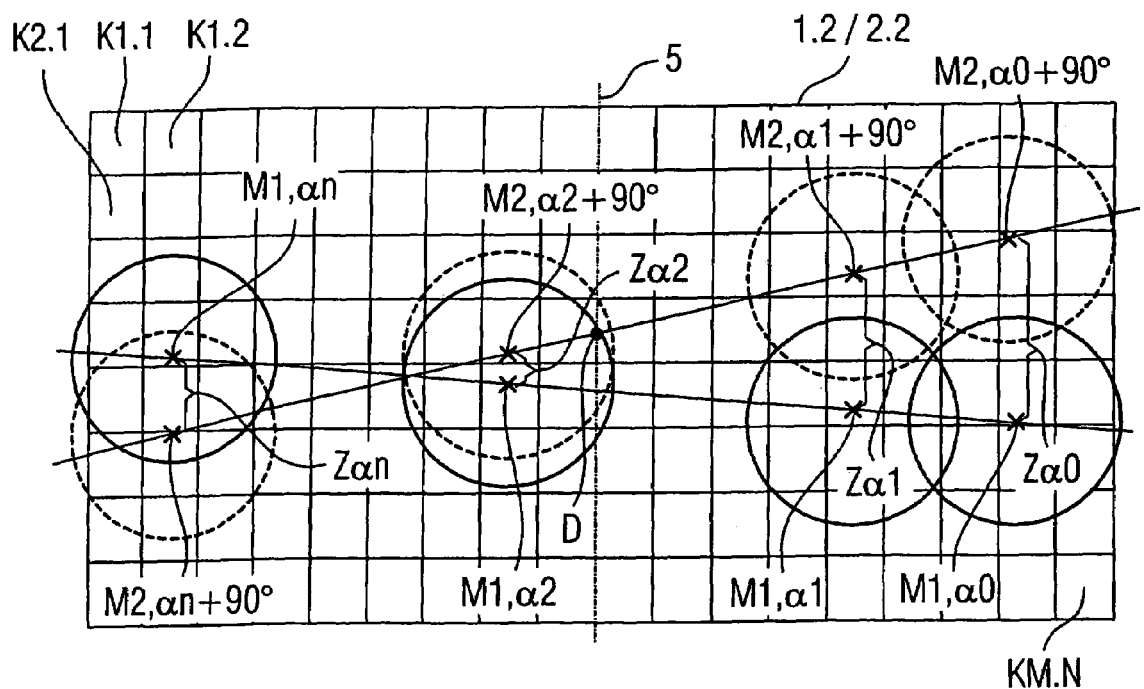
FIG. 5 shows superimposed projection images of the reference object for various rotation angle positions given tilted measurement planes shown in FIG. 4.

For the arrangement shown in FIG. 4 with the reference object R in a common image, FIG. 5, as examples, shows the first projection image R1 associated with the first detector 1.2 and the second projection image R2 associated with the second detector 2.2 for specific rotation angle positions α0, α1, . . . an of both acquisition systems 1.1, 1.2, 2.1, 2.2, with both acquisition systems or measurement planes 14, 16 being tilted around the imaginary connecting line "first radiator 1.2-rotation axis 5" or "second radiator 2.2-rotation axis 5". The projection images R1, R2 of the detectors 1.2, 2.2 are superimposed so that respective, identically-arranged detector elements of both detectors come into congruence.

The projection images R1, R2 of the reference object R are dependent on the respective rotation angle position α0, α1, . . . an of both acquisition systems.

At each rotation angle position α0, α1, . . . an, the respective measurement values M1, α0 . . . M1, an associated with the first detector and the respective measurement value M2, α0 . . . M2, an associated with the second detector can be calculated from the corresponding detector output signals. The determination of the position correction values K1.1 . . . KM.N ensues on the basis of differences of the measurement values M1, α0, . . . M1, an and M2, α0 . . . M2, an that can be calculated from the detector output signals. The difference between the measurement values that are associated with the same projection directions is to be determined. For example, after a 90° rotation of both acquisition systems, the measurement value M2, α0+90° of the second detector 2.2 is associated with the measurement value M1, α0 of the first detector 1.2 at the rotation angle position α0, since in this case the projection directions coincide for the two measurement values M1, α0 and M2, α0+90°.

Each difference represents a displacement vector with which the offset of the projection images R1, R2 can be compensated at a specific position between the two detectors 1.2, 2.2. By measuring the reference object R at specific rotation angle positions α0, α1, . . . an, the displacement vectors necessary for compensation of the image offset are known in this manner for various positions of the detector elements. The determination of the position correction values K1.1 . . . KM.N for all detector element positions can be supplemented by simple two-dimensional linear interpolation for arbitrary positions of the detector elements on the basis of the displacement vectors that can be so determined.

The position correction values K1.1 . . . KM.N of both acquisition systems can be inventively determined for various, substantially constant rotation angle speeds. The storage of the position correction values K1.1 . . . KM.N for a number of rotation angle speeds in a memory 17 associated with the tomography apparatus 3 enables immediate access to the determined position correction values K1.1 . . . KM.N, even during an examination in which the gantry is operated with various rotation angle speeds.

Although modifications and changes may be suggested by those skilled in the art, it is the intention of the inventors to embody within the patent warranted hereon all changes and modifications as reasonably and properly come within the scope of their contribution to the art.

We claim as our invention:

1. An imaging tomography apparatus comprising:
a first data acquisition system disposed in a first measurement plane, comprising a first radiation radiator and a first radiation detector that generates first detector output signals representing absorption of radiation from said first radiation radiator;
a second data acquisition system disposed in a second measurement plane, different from said first measurement plane, comprising a second radiation radiator and a second radiation detector that generates second detector output signals representing absorption of radiation emanating from said second radiation radiator;
said first data acquisition system and said second data acquisition system being mounted for rotation around a rotational axis common to both said first data acquisition system and said second data acquisition system;
a reference object positionable on said rotational axis in each of said first and second measurement planes; and
a calculation unit, supplied with said first detector output signals and said second detector output signals, that calculates, for at least one rotation angle position of said first and second data acquisition systems with said first and second data acquisition systems being rotated at a substantially constant rotation angle speed, a first measurement value from said first detector output signals representing attenuation by said reference object of said radiation emanating from said first radiation radiator, and a second measurement value from said second detector output signals representing attenuation by said reference object of said radiation emanating from said second radiation radiator, and that determines position correction values for each of said first and second measurement planes from said first and second measurement values, representing respective deviations of said first and second measurement planes from respective pre-set positions of said first and second measurement planes, by determining said rotational axis and wherein said calculation unit determines said position correction values as a difference between said first measurement value and said second measurement value.

2. An imaging tomography apparatus as claimed in claim 1 wherein said reference object has a rotationally symmetrical shape.

3. An imaging tomography apparatus as claimed in claim 2 wherein said reference object is a sphere.

4. An imaging tomography apparatus as claimed in claim 1 wherein said first radiation detector comprises multiple first detector elements and wherein said second radiation detector comprises multiple second detector elements, and wherein said reference object attenuates radiation on a number of said first detector elements and on a number of said second detector elements.

5. An imaging tomography apparatus as claimed in claim 1 wherein said calculation unit calculates said first measurement value as a first intensity focal point for said first radiation detector and calculates said second measurement value as a second intensity focal point for said second radiation detector.

6. An imaging tomography apparatus as claimed in claim 1 wherein said calculation unit calculates said position correction values for each of a number of substantially constant rotation angle speeds of said first and second data acquisition systems, and wherein said imaging tomography apparatus comprises a memory connected to said calculation unit for storing the respective position correction values with a designation of the rotation angle speed for which the respective position correction values were obtained.

7. An Imaging tomography apparatus as claimed in claim 1 wherein said first and second data acquisition systems are adapted to interact with an examination subject to respectively obtain first and second image data sets from said examination subject, after said position correction values have been obtained, and wherein said Imaging tomography apparatus comprises an image reconstruction computer, supplied with said first and second image data sets and said position correction values, that calculates an image of the examination subject with the respective first and second image data sets corrected by said position correction values.

8. An imaging tomography apparatus comprising:
a first data acquisition system disposed in a first measurement plane, comprising a first radiation radiator and a first radiation detector that generates first detector output signals representing absorption of radiation from said first radiation radiator;

a second data acquisition system disposed in a second measurement plane, different from said first measurement plane, comprising a second radiation radiator and a second radiation detector that generates second detector output signals representing absorption of radiation emanating from said second radiation radiator;

said first data acquisition system and said second data acquisition system being mounted for rotation around a rotational axis common to both said first data acquisition system and said second data acquisition system;

a reference object positionable outside of said rotational axis in each of said first and second measurement planes: and a calculation unit, supplied with said first detector output signals and said second detector output signals, that calculates, for at least one rotation angle position of said first and second data acquisition systems with said first and second data acquisition systems being rotated at a substantially constant rotation angle speed, a first measurement value from said first detector output signals representing attenuation by said reference object of said radiation emanating from said first radiation radiator, and a second measurement value from said second detector output signals representing attenuation by said reference object of said radiation emanating from said second radiation radiator, and that determines position correction values for each of said first and second measurement planes from said first and second measurement values, representing respective deviations of said first and second measurement planes from respective pre-set positions of said first and second measurement planes by calculating over respective rotations of said first and second data acquisition systems each comprising at least 180°, and determining said position correction values as a difference between said first and second measurement values.

9. An imaging tomography apparatus as claimed in claim 8 wherein said reference object has a rotationally symmetrical shape.

10. An imaging tomography apparatus as claimed in claim 9 wherein said reference object is a sphere.

11. An imaging tomography apparatus as claimed in claim 8 wherein said first radiation detector comprises multiple first detector elements and wherein said second radiation detector comprises multiple second detector elements, and wherein said reference object attenuates radiation on a number of said first detector elements and on a number of said second detector elements.

12. An imaging tomography apparatus as claimed in claim 8 wherein said calculation unit calculates said first measurement value as a first intensity focal point for said first radiation detector and calculates said second measurement value as a second intensity focal point for said second radiation detector.

13. An imaging tomography apparatus as claimed in claim 8 wherein said calculation unit calculates said position correction values for each of a number of substantially constant rotation angle speeds of said first and second data acquisition systems, and wherein said imaging tomography apparatus comprises a memory connected to said calculation unit for storing the respective position correction values with a designation of the rotation angle speed for which the respective position correction values were obtained.

14. An imaging tomography apparatus as claimed in claim 8 wherein said first and second data acquisition systems are adapted to interact with an examination subject to respectively obtain first and second image data sets from said examination subject, after said position correction values have been obtained, and wherein said imaging tomography apparatus comprises an image reconstruction computer, supplied with said first and second image data sets and said position correction values, that calculates an image of the examination subject with the respective first and second image data sets corrected by said position correction values.

15. A method for operating an imaging tomography apparatus comprising a first data acquisition system disposed in a first measurement plane, comprising a first radiation radiator and a first radiation detector that generates first detector output signals representing absorption of radiation from said first radiation radiator, a second data acquisition system disposed in a second measurement plane, different from said first measurement plane, comprising a second radiation radiator and a second radiation detector that generates second detector output signals representing absorption of radiation emanating from said second radiation radiator, said first data acquisition system and said second data acquisition system being mounted for rotation around a rotational axis common to both said first data acquisition system and said second data acquisition system, said method comprising the steps of:

positioning a single reference object on said rotational axis simultaneously in each of said first and second measurement planes;

electronically calculating, for at least one rotation angle position of said first and second data acquisition systems with said first and second data acquisition systems being rotated at a substantially constant rotation angle speed, a first measurement value from said first detector output signals representing attenuation by said reference object of said radiation emanating from said first radiation radiator, and a second measurement value from said second detector output signals representing attenuation by said reference object of said radiation emanating from said second radiation radiator; and electronically determining position correction values for each of said first and second measurement planes from said first and second measurement values, representing respective deviations of said first and second measurement planes from respective pre-set positions of said first and second measurement planes by determining said position correction values as a difference between said first measurement value and said second measurement value.

16. A method as claimed in claim 15 comprising employing an object as said reference object having a rotationally symmetrical shape.

17. A method as claimed in claim 16 comprising employing a sphere as said reference object.

18. A method as claimed in claim 15 comprising electronically calculating said first measurement value as a first intensity focal point for said first radiation detector and electronically calculating said second measurement value as a second intensity focal point for said second radiation detector.

19. A method as claimed in claim 15 comprising electronically calculating said position correction values for each of a number of substantially constant rotation angle speeds of said first and second data acquisition systems, and electronically storing the respective position correction values with a designation of the rotation angle speed for which the respective position correction values were obtained.

20. A method as claimed in claim 15 comprising irradiating an examination subject with said first and second data acquisition systems to respectively obtain first and second image data sets from said examination subject, after said position correction values have been obtained, and electronically reconstructing an image of the examination subject with the respective first and second image data sets corrected by said position correction values.

21. A method for operating an imaging tomography apparatus comprising a first data acquisition system disposed in a first measurement plane, comprising a first radiation radiator and a first radiation detector that generates first detector output signals representing absorption of radiation from said first radiation radiator, a second data acquisition system disposed in a second measurement plane, different from said first measurement plane, comprising a second radiation radiator and a second radiation detector that generates second detector output signals representing absorption of radiation emanating from said second radiation radiator, said first data acquisition system and said second data acquisition system being mounted for rotation around a rotational axis common to both said first data acquisition system and said second data acquisition system, said method comprising the steps of:

positioning a single reference object outside of said rotational axis in each of said first and second measurement planes;

electronically calculating, for at least one rotation angle position of said first and second data acquisition systems with said first and second data acquisition systems being rotated at a substantially constant rotation angle speed, a first measurement value from said first detector output signals representing attenuation by said reference object of said radiation emanating from said first radiation radiator, and a second measurement value from said second detector output signals representing attenuation by said reference object of said radiation emanating from said second radiation radiator; and electronically determining position correction values for each of said first and second measurement planes from said first and second measurement values, representing respective deviations of said first and second measurement planes from respective pre-set positions of said first and second measurement planes by calculating said first and second measurement values over respective rotations of said first and second data acquisition systems each comprising at least 180°, and determining said position correction values as a difference between said first and second measurement values.

22. An imaging tomography apparatus as claimed in claim 21 wherein said calculation unit calculates said position correction values for each of a number of substantially constant rotation angle speeds of said first and second data acquisition systems, and wherein said imaging tomography apparatus comprises a memory connected to said calculation unit for storing the respective position correction values with a designation of the rotation angle speed for which the respective position correction values were obtained.

23. An imaging tomography apparatus as claimed in claim 22 wherein said first and second data acquisition systems are adapted to interact with an examination subject to respectively obtain first and second image data sets from said examination subject, after said position correction values have been obtained, and wherein said imaging tomography apparatus comprises an image reconstruction computer, supplied with said first and second image data sets and said position correction values, that calculates an image of the examination subject with the respective first and second image data sets corrected by said position correction values.

24. A method as claimed in claim 21 comprising electronically calculating said first measurement value as a first intensity focal point for said first radiation detector and electronically calculating said second measurement value as a second intensity focal point for said second radiation detector.

25. A method as claimed in claim 21 comprising electronically calculating said position correction values for each of a number of substantially constant rotation angle speeds of said first and second data acquisition systems, and electronically storing the respective position correction values with a designation of the rotation angle speed for which the respective position correction values were obtained.

26. A method as claimed in claim 21 comprising irradiating an examination subject with said first and second data acquisition systems to respectively obtain first and second image data sets from said examination subject, after said position correction values have been obtained, and electronically reconstructing an image of the examination subject with the respective first and second image data sets corrected by said position correction values.

* * * * *